(12) United States Patent
Song

(10) Patent No.: US 10,945,967 B2
(45) Date of Patent: Mar. 16, 2021

(54) FORMULATIONS OF A TRANSDERMAL PATCH FOR PAIN MANAGEMENT

(71) Applicant: Jae Wang. Song, Yorba Linda, CA (US)

(72) Inventor: Jae Wang. Song, Yorba Linda, CA (US)

( * ) Notice: Subject to any disclaimer, the term of this patent is extended or adjusted under 35 U.S.C. 154(b) by 0 days.

(21) Appl. No.: 15/732,889

(22) Filed: Jan. 16, 2018

(65) Prior Publication Data

US 2019/0216745 A1    Jul. 18, 2019

Related U.S. Application Data

(60) Provisional application No. 62/603,388, filed on May 30, 2017.

(51) Int. Cl.
| | |
|---|---|
| *A61K 9/70* | (2006.01) |
| *A61K 9/107* | (2006.01) |
| *A61P 29/02* | (2006.01) |
| *A61K 31/105* | (2006.01) |
| *A61K 36/324* | (2006.01) |
| *A61K 31/352* | (2006.01) |

(52) U.S. Cl.
CPC .......... *A61K 9/7038* (2013.01); *A61K 9/1075* (2013.01); *A61K 9/7084* (2013.01); *A61K 31/105* (2013.01); *A61K 31/352* (2013.01); *A61K 36/324* (2013.01); *A61P 29/02* (2018.01)

(58) Field of Classification Search
CPC .. A61K 9/7038; A61K 31/352; A61K 36/324; A61K 9/1075; A61K 31/105; A61P 29/02
See application file for complete search history.

(56) References Cited

U.S. PATENT DOCUMENTS

| | | | | |
|---|---|---|---|---|
| 6,534,086 B1 * | 3/2003 | Krumhar | ............... | A61K 36/324 424/435 |
| 2009/0042950 A1 * | 2/2009 | Pandya | ................ | A61K 9/0014 514/343 |
| 2013/0177611 A1 * | 7/2013 | Kaplan | ................ | A61K 9/7007 424/400 |
| 2015/0297556 A1 * | 10/2015 | Smith | .................. | A61K 31/352 424/449 |

* cited by examiner

*Primary Examiner* — Matthew P Coughlin
*Assistant Examiner* — Thurman Wheeler
(74) *Attorney, Agent, or Firm* — Law Office of Ilya Libenzon

(57) ABSTRACT

Various formulations (to be used in the form of a single-segment or multi-segment transdermal patch) of bioactive compounds for pain management are described/disclosed. The multi-segmented transdermal patch can include one or more compatible bioactive compounds in each segment. Furthermore, formulations may include silk fibroin and/or microemulsion/nanoemulsion of bioactive compounds and/or microencapsulation/nanoencapsulation of bioactive compounds.

12 Claims, No Drawings

FORMULATIONS OF A TRANSDERMAL PATCH FOR PAIN MANAGEMENT

This patent application claims priority to U.S. Provisional Patent Application Ser. No. 62/603,388 entitled "FORMULATIONS OF A TRANSDERMAL PATCH FOR PAIN MANAGEMENT", filed on May 30, 2017.

Chronic pain represents an emerging public health issue of massive proportions, particularly in view of aging populations in industrialized nations. About 19% of adults (about 38 million) in USA have chronic pain.

The present application discloses various compositions (as listed below) of bioactive compounds of a pressure sensitive transdermal patch (e.g., a pressure sensitive single-layer transdermal/multi-layer/reservoir transdermal patch) for pain management. Among the benefits of a pressure sensitive transdermal patch are reduced gastro-intestinal incompatibility, steady dosage rate/flux rate, self-administration and non-invasive procedure.

Pressure Sensitive Single-Layer Transdermal Patch: The adhesive layer of the pressure sensitive single-layer transdermal patch contains bioactive compounds. The adhesive layer not only adheres with the various layers together, along with the entire system to the skin, but also is responsible for the releasing of the bioactive compounds. The adhesive layer is surrounded by a temporary liner and a backing.

Pressure Sensitive Multi-Layer Transdermal Patch: One of the layers of the pressure sensitive multi-layer transdermal patch is for immediate release of bioactive compounds and other layer is for control release of the bioactive compounds from an embedded reservoir. It has both a temporary liner-layer and a permanent backing. The release of the bioactive compounds depends on membrane permeability and diffusion of drug molecules.

Pressure Sensitive Reservoir Transdermal Patch: Unlike the pressure sensitive single-layer transdermal patch and pressure sensitive multi-layer transdermal patch, the pressure sensitive reservoir transdermal patch has a separate layer of bioactive compounds in solution or suspension (separated by an adhesive layer). The reservoir of the bioactive compounds is encapsulated in a shallow compartment, which molded from a bioactives-impermeable metallic plastic laminate with rate-controlling polymer (e.g., vinyl acetate) membrane on one surface. This patch is also backed by the backing layer.

The adhesive (e.g., polyacrylates, polyisobutylene or silicon based adhesive) of the pressure sensitive single-layer transdermal/multi-layer plays a critical role for establishing (a) flux rate of the bioactive compounds to skin, (b) adhesion to skin, (c) stability/shelf life, (d) peel strength and (e) skin irritation.

Furthermore, a patch can utilize low-level electrical energy to transport bioactive compounds through the skin in a controlled manner.

Additionally, an array of micro-needles located on the surface of a pressure sensitive transdermal patch that comes in contact with the skin can be utilized to deliver bioactive compounds.

TABLE 1

Pharmaceutical Formulation [Active Composition Of Bioactive Compounds]

| | WT % |
|---|---|
| Botanical | |
| *Boswellia serrata* Extract | 20% |
| Chemicals | |
| Astaxanthin | 2.5% |
| Capsaicin | 5% |
| Pure* CBD (Or CBD Pro-Drug) | 40% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 2

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Pure* CBD (Or CBD Pro-Drug) | 42.5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 3

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Pure* CBD (Or CBD Pro-Drug) | 47.5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 4

| Pharmaceutical Formulation [Active Composition Of Bioactive Compounds] | WT % |
|---|---|
| Botanical | |
| *Boswellia serrata* Extract | 20% |
| Chemicals | |
| Capsaicin | 5% |
| Pure* CBD (Or CBD Pro-Drug) | 52.5% |
| Glucosamine Hydrochloride Or Glucosamine Sulfate | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 5

| Pharmaceutical Formulation [Active Composition Of Bioactive Compounds] | WT % |
|---|---|
| Botanical | |
| *Boswellia serrata* Extract | 20% |
| Chemicals | |
| Capsaicin | 5% |
| Pure* CBD (Or CBD Pro-Drug) | 57.5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 6

| Pharmaceutical Formulation [Active Composition Of Bioactive Compounds] | WT % |
|---|---|
| Botanical | |
| *Boswellia serrata* Extract | 20% |
| Chemicals | |
| Capsaicin | 5% |
| Pure* CBD (Or CBD Pro-Drug) | 57.5% |
| Lidocaine Hydrochloride | 7.5% |
| Methylsufonlymethane (MSM) | 5% |
| Menthol | 5% |
| Total | 100% |

TABLE 7

| Pharmaceutical Formulation [Active Composition Of Bioactive Compounds] | WT % |
|---|---|
| Botanical | |
| *Boswellia serrata* Extract | 25% |
| Chemicals | |
| Capsaicin | 5% |
| Pure* CBD (Or CBD Pro-Drug) | 57.5% |
| Lidocaine Hydrochloride | 7.5% |
| Menthol | 5% |
| Total | 100% |

TABLE 8

| Pharmaceutical Formulation [Active Composition Of Bioactive Compounds] | WT % |
|---|---|
| Botanical | |
| *Boswellia serrata* Extract | 30% |
| Chemicals | |
| Capsaicin | 5% |
| Pure* CBD (Or CBD Pro-Drug) | 57.5% |
| Lidocaine Hydrochloride | 7.5% |
| Total | 100% |

TABLE 9

| Pharmaceutical Formulation [Active Composition Of Bioactive Compounds] | WT % |
|---|---|
| Botanical | |
| *Boswellia serrata* Extract | 30% |
| Chemicals | |
| Capsaicin | 5% |
| Pure* CBD (Or CBD Pro-Drug) | 65% |
| Total | 100% |

TABLE 10

| Pharmaceutical Formulation [Active Composition Of Bioactive Compounds] | WT % |
|---|---|
| Botanical | |
| *Boswellia serrata* Extract | 30% |
| Chemicals | |
| Pure* CBD (Or CBD Pro-Drug) | 70% |
| Total | 100% |

TABLE 11

Pharmaceutical Formulation [Active Composition Of Bioactive Compounds]

| Chemicals | WT % |
|---|---|
| Capsaicin | 5% |
| Pure* CBD (Or CBD Pro-Drug) | 95% |
| Total | 100% |

TABLE 12

Pharmaceutical Formulation [Active Composition Of Bioactive Compounds]

| | WT % |
|---|---|
| Botanical | |
| *Boswellia serrata* Extract | 20% |
| Chemicals | |
| Astaxanthin | 2.5% |
| Capsaicin | 5% |
| Pure* CBD (Or CBD Pro-Drug) | 35% |
| Pure* CBC (Or CBC Pro-Drug) | 5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 13

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Pure* CBD (Or CBD Pro-Drug) | 37.5% |
| Pure* CBC (Or CBC Pro-Drug) | 5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 14

Pharmaceutical Formulation [Active Composition Of Bioactive Compounds]

| | WT % |
|---|---|
| Botanical | |
| *Boswellia serrata* Extract | 20% |

TABLE 14-continued

Pharmaceutical Formulation [Active Composition Of Bioactive Compounds]

| | WT % |
|---|---|
| Chemicals | |
| Capsaicin | 5% |
| Pure* CBD (Or CBD Pro-Drug) | 42.5% |
| Pure* CBC (Or CBC Pro-Drug) | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 15

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Pure* CBD (Or CBD Pro-Drug) | 47.5% |
| Pure* CBC (Or CBC Pro-Drug) | 5% |
| Glucosamine Hydrochloride Or Glucosamine Sulfate | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 16

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Pure* CBD (Or CBD Pro-Drug) | 52.5% |
| Pure* CBC (Or CBC Pro-Drug) | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 17

Pharmaceutical Formulation [Active Composition Of Bioactive Compounds]

| | WT % |
|---|---|
| Botanical | |
| *Boswellia serrata* Extract | 20% |

TABLE 17-continued

Pharmaceutical Formulation [Active Composition Of Bioactive Compounds]

|  | WT % |
|---|---|
| Chemicals | |
| Capsaicin | 5% |
| Pure* CBD (Or CBD Pro-Drug) | 57.5% |
| Pure* CBC (Or CBC Pro-Drug) | 5% |
| Lidocaine Hydrochloride | 2.5% |
| Methylsufonlymethane (MSM) | 5% |
| Menthol | 5% |
| Total | 100% |

TABLE 18

Pharmaceutical Formulation [Active Composition Of Bioactive Compounds]

|  | WT % |
|---|---|
| Botanical | |
| *Boswellia serrata* Extract | 25% |
| Chemicals | |
| Capsaicin | 5% |
| Pure* CBD (Or CBD Pro-Drug) | 57.5% |
| Pure* CBC (Or CBC Pro-Drug) | 5% |
| Lidocaine Hydrochloride | 2.5% |
| Menthol | 5% |
| Total | 100% |

TABLE 19

Pharmaceutical Formulation [Active Composition Of Bioactive Compounds]

|  | WT % |
|---|---|
| Botanical | |
| *Boswellia serrata* Extract | 30% |
| Chemicals | |
| Capsaicin | 5% |
| Pure* CBD (Or CBD Pro-Drug) | 57.5% |
| Pure* CBC (Or CBC Pro-Drug) | 5% |
| Lidocaine Hydrochloride | 2.5% |
| Total | 100% |

TABLE 20

Pharmaceutical Formulation [Active Composition Of Bioactive Compounds]

|  | WT % |
|---|---|
| Botanical | |
| *Boswellia serrata* Extract | 25% |
| Chemicals | |
| Capsaicin | 5% |
| Pure* CBD (Or CBD Pro-Drug) | 65% |
| Pure* CBC (Or CBC Pro-Drug) | 5% |
| Total | 100% |

TABLE 21

Pharmaceutical Formulation [Active Composition Of Bioactive Compounds]

|  | WT % |
|---|---|
| Botanical | |
| *Boswellia serrata* Extract | 25% |
| Chemicals | |
| Pure* CBD (Or CBD Pro-Drug) | 70% |
| Pure* CBC (Or CBC Pro-Drug) | 5% |
| Total | 100% |

TABLE 22

Pharmaceutical Formulation [Active Composition Of Bioactive Compounds]

| Chemicals | WT % |
|---|---|
| Capsaicin | 5% |
| Pure* CBD (Or CBD Pro-Drug) | 90% |
| Pure* CBC (Or CBC Pro-Drug) | 5% |
| Total | 100% |

TABLE 23

Pharmaceutical Formulation [Active Composition Of Bioactive Compounds]

|  | WT % |
|---|---|
| Botanical | |
| *Boswellia serrata* Extract | 20% |
| Chemicals | |
| Astaxanthin | 2.5% |
| Capsaicin | 5% |
| Silk Fibroin Loaded With Pure* CBD (Or CBD Pro-Drug) | 40% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 24

Pharmaceutical Formulation [Active Composition Of Bioactive Compounds]

|  | WT % |
|---|---|
| Botanical | |
| *Boswellia serrata* Extract | 20% |
| Chemicals | |
| Capsaicin | 5% |
| Silk Fibroin Loaded With Pure* CBD (Or CBD Pro-Drug) | 42.5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |

TABLE 24-continued

Pharmaceutical Formulation [Active Composition Of Bioactive Compounds]

| | WT % |
|---|---|
| Menthol | 5% |
| S-Adenosyl Methionine (SAM) | 5% |
| Total | 100% |

TABLE 25

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Silk Fibroin Loaded With Pure* CBD (Or CBD Pro-Drug) | 47.5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 26

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Silk Fibroin Loaded With Pure* CBD (Or CBD Pro-Drug) | 52.5% |
| Glucosamine Hydrochloride Or Glucosamine Sulfate | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 27

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Silk Fibroin Loaded With Pure* CBD (Or CBD Pro-Drug) | 57.5% |
| Lidocaine Hydrochloride | 2.5% |
| Methylsufonlymethane (MSM) | 5% |

TABLE 27-continued

Pharmaceutical Formulation [Active Composition Of Bioactive Compounds]

| | WT % |
|---|---|
| Menthol | 5% |
| S-Adenosyl Methionine (SAM) | 5% |
| Total | 100% |

TABLE 28

Pharmaceutical Formulation [Active Composition Of Bioactive Compounds]

| | WT % |
|---|---|
| Botanical | |
| *Boswellia serrata* Extract | 20% |
| Chemicals | |
| Capsaicin | 5% |
| Silk Fibroin Loaded With Pure* CBD (Or CBD Pro-Drug) | 57.5% |
| Lidocaine Hydrochloride | 7.5% |
| Methylsufonlymethane (MSM) | 5% |
| Menthol | 5% |
| Total | 100% |

TABLE 29

Pharmaceutical Formulation [Active Composition Of Bioactive Compounds]

| | WT % |
|---|---|
| Botanical | |
| *Boswellia serrata* Extract | 25% |
| Chemicals | |
| Capsaicin | 5% |
| Silk Fibroin Loaded With Pure* CBD (Or CBD Pro-Drug) | 57.5% |
| Lidocaine Hydrochloride | 7.5% |
| Menthol | 5% |
| Total | 100% |

TABLE 30

Pharmaceutical Formulation [Active Composition Of Bioactive Compounds]

| | WT % |
|---|---|
| Botanical | |
| *Boswellia serrata* Extract | 30% |
| Chemicals | |
| Capsaicin | 5% |
| Silk Fibroin Loaded With Pure* CBD (Or CBD Pro-Drug) | 57.5% |
| Lidocaine Hydrochloride | 7.5% |
| Total | 100% |

TABLE 31

Pharmaceutical Formulation [Active Composition Of Bioactive Compounds]

| | WT % |
|---|---|
| Botanical | |
| Boswellia serrata Extract | 30% |
| Chemicals | |
| Capsaicin | 5% |
| Pure* CBD (Or CBD Pro-Drug) | 65% |
| Total | 100% |

TABLE 32

Pharmaceutical Formulation [Active Composition Of Bioactive Compounds]

| | WT % |
|---|---|
| Botanical | |
| Boswellia serrata Extract | 30% |
| Chemicals | |
| Silk Fibroin Loaded With Pure* CBD (Or CBD Pro-Drug) | 70% |
| Total | 100% |

TABLE 33

Pharmaceutical Formulation [Active Composition Of Bioactive Compounds]

| Chemicals | WT % |
|---|---|
| Capsaicin | 5% |
| Silk Fibroin Loaded With Pure* CBD (Or CBD Pro-Drug) | 95% |
| Total | 100% |

TABLE 34

Pharmaceutical Formulation [Active Composition Of Bioactive Compounds]

| Chemicals | WT % |
|---|---|
| Silk Fibroin Loaded With Pure* CBD (Or CBD Pro-Drug) | 100% |
| Total | 100% |

TABLE 35

Pharmaceutical Formulation [Active Composition Of Bioactive Compounds]

| | WT % |
|---|---|
| Botanical | |
| Boswellia serrata Extract | 20% |
| Chemicals | |
| Astaxanthin | 2.5% |
| Capsaicin | 5% |
| Silk Fibroin Loaded With Pure* Pure* CBD (Or CBD Pro-Drug) | 35% |
| Silk Fibroin Loaded With Pure* Pure* CBC (Or CBC Pro-Drug) | 5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 36

Pharmaceutical Formulation [Active Composition Of Bioactive Compounds]

| | WT % |
|---|---|
| Botanical | |
| Boswellia serrata Extract | 20% |
| Chemicals | |
| Capsaicin | 5% |
| Silk Fibroin Loaded With Pure* Pure* CBD (Or CBD Pro-Drug) | 37.5% |
| Silk Fibroin Loaded With Pure* Pure* CBC (Or CBC Pro-Drug) | 5% |
| Chondroitin Sulfate | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 37

Pharmaceutical Formulation [Active Composition Of Bioactive Compounds]

| | WT % |
|---|---|
| Botanical | |
| Boswellia serrata Extract | 20% |
| Chemicals | |
| Capsaicin | 5% |
| Silk Fibroin Loaded With Pure* Pure* CBD (Or CBD Pro-Drug) | 42.5% |
| Silk Fibroin Loaded With Pure* Pure* CBC (Or CBC Pro-Drug) | 5% |
| Glucosamine Hydrochloride Or Glucosamine Sulfate | 5% |
| Hyaluronic Acid | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 38

Pharmaceutical Formulation [Active Composition Of Bioactive Compounds]

| | WT % |
|---|---|
| Botanical | |
| Boswellia serrata Extract | 20% |
| Chemicals | |
| Capsaicin | 5% |
| Silk Fibroin Loaded With Pure* Pure* CBD (Or CBD Pro-Drug) | 47.5% |
| Silk Fibroin Loaded With Pure* Pure* CBC (Or CBC Pro-Drug) | 5% |
| Glucosamine Hydrochloride Or Glucosamine Sulfate | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 39

Pharmaceutical Formulation [Active Composition Of Bioactive Compounds]

| | WT % |
|---|---|
| Botanical | |
| Boswellia serrata Extract | 20% |
| Chemicals | |
| Capsaicin | 5% |
| Silk Fibroin Loaded With Pure* Pure* CBD (Or CBD Pro-Drug) | 52.5% |
| Silk Fibroin Loaded With Pure* Pure* CBC (Or CBC Pro-Drug) | 5% |
| Lidocaine Hydrochloride | 2.5% |
| Methylsufonlymethane (MSM) | 5% |
| Menthol | 5% |
| S-Adenosyl Methionine (SAM) | 5% |
| Total | 100% |

TABLE 40

Pharmaceutical Formulation [Active Composition Of Bioactive Compounds]

| | WT % |
|---|---|
| Botanical | |
| Boswellia serrata Extract | 20% |
| Chemicals | |
| Capsaicin | 5% |
| Silk Fibroin Loaded With Pure* Pure* CBD (Or CBD Pro-Drug) | 57.5% |
| Silk Fibroin Loaded With Pure* Pure* CBC (Or CBC Pro-Drug) | 5% |
| Lidocaine Hydrochloride | 2.5% |
| Methylsufonlymethane (MSM) | 5% |
| Menthol | 5% |
| Total | 100% |

TABLE 41

Pharmaceutical Formulation [Active Composition Of Bioactive Compounds]

| | WT % |
|---|---|
| Botanical | |
| Boswellia serrata Extract | 25% |
| Chemicals | |
| Capsaicin | 5% |
| Silk Fibroin Loaded With Pure* Pure* CBD (Or CBD Pro-Drug) | 57.5% |
| Silk Fibroin Loaded With Pure* Pure* CBC (Or CBC Pro-Drug) | 5% |
| Lidocaine Hydrochloride | 2.5% |
| Menthol | 5% |
| Total | 100% |

TABLE 42

Pharmaceutical Formulation [Active Composition Of Bioactive Compounds]

| | WT % |
|---|---|
| Botanical | |
| Boswellia serrata Extract | 30% |
| Chemicals | |
| Capsaicin | 5% |
| Silk Fibroin Loaded With Pure* Pure* CBD (Or CBD Pro-Drug) | 57.5% |
| Silk Fibroin Loaded With Pure* Pure* CBC (Or CBC Pro-Drug) | 5% |
| Lidocaine Hydrochloride | 2.5% |
| Total | 100% |

TABLE 43

Pharmaceutical Formulation [Active Composition Of Bioactive Compounds]

| | WT % |
|---|---|
| Botanical | |
| Boswellia serrata Extract | 25% |
| Chemicals | |
| Capsaicin | 5% |
| Silk Fibroin Loaded With Pure* Pure* CBD (Or CBD Pro-Drug) | 65% |
| Silk Fibroin Loaded With Pure* Pure* CBC (Or CBC Pro-Drug) | 5% |
| Total | 100% |

TABLE 44

Pharmaceutical Formulation [Active Composition Of Bioactive Compounds]

| | WT % |
|---|---|
| Botanical | |
| Boswellia serrata Extract | 25% |

TABLE 44-continued

Pharmaceutical Formulation [Active Composition Of Bioactive Compounds]

| | WT % |
|---|---|
| Chemicals | |
| Silk Fibroin Loaded With Pure* Pure* CBD (Or CBD Pro-Drug) | 70% |
| Silk Fibroin Loaded With Pure* Pure* CBC (Or CBC Pro-Drug) | 5% |
| Total | 100% |

TABLE 45

Pharmaceutical Formulation [Active Composition Of Bioactive Compounds]

| Chemicals | WT % |
|---|---|
| Capsaicin | 5% |
| Silk Fibroin Loaded With Pure* Pure* CBD (Or CBD Pro-Drug) | 90% |
| Silk Fibroin Loaded With Pure* Pure* CBC (Or CBC Pro-Drug) | 5% |
| Total | 100% |

TABLE 46

Pharmaceutical Formulation [Active Composition Of Bioactive Compounds]

| Chemicals | WT % |
|---|---|
| Silk Fibroin Loaded With Pure* Pure* CBD (Or CBD Pro-Drug) | 90% |
| Silk Fibroin Loaded With Pure* Pure* CBC (Or CBC Pro-Drug) | 10% |
| Total | 100% |

TABLE 47

Pharmaceutical Formulation [Active Composition Of Bioactive Compounds]

| | WT % |
|---|---|
| Botanical | |
| *Boswellia serrata* Extract | 55% |
| Chemicals | |
| Astaxanthin | 5% |
| Capsaicin | 5% |
| Chondroitin Sulfate | 5% |
| Glucosamine Hydrochloride Or Glucosamine Sulfate | 5% |
| Hyaluronic Acid | 5% |
| Lidocaine Hydrochloride | 5% |
| Methylsufonlymethane (MSM) | 5% |
| Menthol | 5% |
| S-Adenosyl Methionine (SAM) | 5% |
| Total | 100% |

TABLE 48

Pharmaceutical Formulation [Active Composition Of Bioactive Compounds]

| | WT % |
|---|---|
| Botanical | |
| *Boswellia serrata* Extract | 55% |

TABLE 48-continued

Pharmaceutical Formulation [Active Composition Of Bioactive Compounds]

| | WT % |
|---|---|
| Chemicals | |
| Capsaicin | 5% |
| Chondroitin Sulfate | 7.5% |
| Glucosamine Hydrochloride Or Glucosamine Sulfate | 7.5% |
| Hyaluronic Acid | 5% |
| Lidocaine Hydrochloride | 5% |
| Methylsufonlymethane (MSM) | 5% |
| Menthol | 5% |
| S-Adenosyl Methionine (SAM) | 5% |
| Total | 100% |

TABLE 49

Pharmaceutical Formulation [Active Composition Of Bioactive Compounds]

| | WT % |
|---|---|
| Botanical | |
| *Boswellia serrata* Extract | 60% |
| Chemicals | |
| Capsaicin | 5% |
| Glucosamine Hydrochloride Or Glucosamine Sulfate | 10% |
| Hyaluronic Acid | 5% |
| Lidocaine Hydrochloride | 5% |
| Methylsufonlymethane (MSM) | 5% |
| Menthol | 5% |
| S-Adenosyl Methionine (SAM) | 5% |
| Total | 100% |

TABLE 50

Pharmaceutical Formulation [Active Composition Of Bioactive Compounds]

| | WT % |
|---|---|
| Botanical | |
| *Boswellia serrata* Extract | 60% |
| Chemicals | |
| Capsaicin | 5% |
| Glucosamine Hydrochloride Or Glucosamine Sulfate | 10% |
| Hyaluronic Acid | 5% |
| Lidocaine Hydrochloride | 5% |
| Methylsufonlymethane (MSM) | 10% |
| Menthol | 5% |
| Total | 100% |

TABLE 51

Pharmaceutical Formulation [Active Composition Of Bioactive Compounds]

| | WT % |
|---|---|
| Botanical | |
| *Boswellia serrata* Extract | 60% |

TABLE 51-continued

Pharmaceutical Formulation [Active Composition Of Bioactive Compounds]

| | WT % |
|---|---|
| Chemicals | |
| Capsaicin | 5% |
| Glucosamine Hydrochloride Or Glucosamine Sulfate | 10% |
| Hyaluronic Acid | 10% |
| Lidocaine Hydrochloride | 5% |
| Methylsufonlymethane (MSM) | 10% |
| Total | 100% |

TABLE 52

Pharmaceutical Formulation [Active Composition Of Bioactive Compounds]

| | WT % |
|---|---|
| Botanical | |
| *Boswellia serrata* Extract | 65% |
| Chemicals | |
| Capsaicin | 5% |
| Glucosamine Hydrochloride Or Glucosamine Sulfate | 10% |
| Hyaluronic Acid | 10% |
| Methylsufonlymethane (MSM) | 10% |
| Total | 100% |

TABLE 53

Pharmaceutical Formulation [Active Composition Of Bioactive Compounds]

| | WT % |
|---|---|
| Botanical | |
| *Boswellia serrata* Extract | 70% |
| Chemicals | |
| Glucosamine Hydrochloride Or Glucosamine Sulfate | 10% |
| Hyaluronic Acid | 10% |
| Methylsufonlymethane (MSM) | 10% |
| Total | 100% |

TABLE 54

Pharmaceutical Formulation [Active Composition Of Bioactive Compounds]

| | WT % |
|---|---|
| Botanical | |
| *Boswellia serrata* Extract | 80% |
| Chemicals | |
| Glucosamine Hydrochloride Or Glucosamine Sulfate | 10% |
| Methylsufonlymethane (MSM) | 10% |
| Total | 100% |

TABLE 55

Pharmaceutical Formulation [Active Composition Of Bioactive Compounds]

| | WT % |
|---|---|
| Botanical | |
| *Boswellia serrata* Extract | 70% |
| Chemicals | |
| Glucosamine Hydrochloride Or Glucosamine Sulfate | 15% |
| Methylsufonlymethane (MSM) | 15% |
| Total | 100% |

TABLE 56

Pharmaceutical Formulation [Active Composition Of Bioactive Compounds]

| | WT % |
|---|---|
| Botanical | |
| *Boswellia serrata* Extract | 70% |
| Chemicals | |
| Glucosamine Hydrochloride Or Glucosamine Sulfate | 30% |
| Total | 100% |

Cannabidiol (CBD), a bioactive compound of marijuana plant (*Cannabis sativa* or *Cannabis indica* or its synthetic analogue) or its prodrug can blunt beta-amyloid induced neuroinflammation by suppressing IL-1beta and iNOS expression.

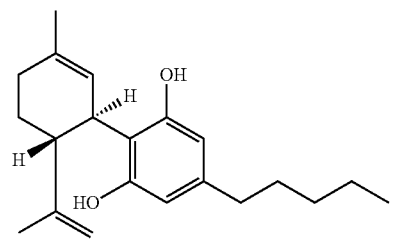 [SMILES: C=C(C)[C@@H]1CCC(C)=C[C@H]1c1c(O)cc(CCCCC)cc1O]

Molecular Structure of Cannabidiol (CBD)

Cannabichromene (CBC), a bioactive compound of marijuana plant (*Cannabis sativa* or *Cannabis indica*). Its molecular structure is described below.

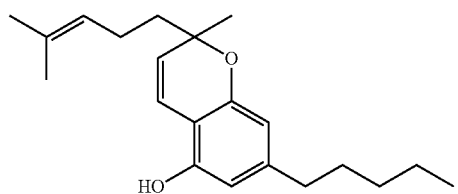

Molecular Structure of Cannabichromene (CBC)

THC content in CBD or CBC is below the federally approved legal limit.

Weight % of the bioactive compound(s) in the pharmaceutical formulations of Table-1 through Table-56 can vary +/−20%

To increase permeation the bioactive compound(s) in the pharmaceutical formulations of Table-1 through Table-56, wherein the bioactive compound(s) in the pharmaceutical formulations of Table-1 through Table-56 is embedded with an adhesive (of a pressure sensitive transdermal patch), a permeation enhancement compound (e.g., oleic acid/eucalyptol oil) can be utilized, a passive compound in the pharmaceutical formulations of Table-1 through Table-56

To reduce chemical reaction between bioactive compounds in the pharmaceutical formulations of Table-1 through Table-56, lecithin (e.g., soy-derived lecithin) a multi-segmented transdermal patch can be utilized instead of a single segmented patch, wherein each segment of the multi-segmented transdermal patch can include one or more compatible bioactive compounds.

To reduce chemical reaction between bioactive compounds in the pharmaceutical formulations of Table-1 through Table-56, lecithin (e.g., soy-derived lecithin) in Table-1 through Table-56 can be utilized.

To increase bioavailability the bioactive compound(s) in the pharmaceutical formulations of Table-1 through Table-56, a microemulsion/nanoemulsion of the bioactive compound(s) in Table-1 through Table-56 can be utilized.

To increase bioavailability the bioactive compound(s) in the pharmaceutical formulations of Table-1 through Table-56, a microencapsulation/nanoencapsulation of the bioactive compound(s) in the pharmaceutical formulations of Table-1 through Table-56 can be utilized.

For sustained delivery of the bioactive compound(s) in the pharmaceutical formulations of Table-1 through Table-56, a microencapsulation/nanoencapsulation of the bioactive compound(s) in the pharmaceutical formulations of Table-1 through Table-56 can be utilized.

For controlled delivery of the bioactive compound(s) in the pharmaceutical formulations of Table-1 through Table-56, a microencapsulation/nanoencapsulation of the bioactive compound(s) in the pharmaceutical formulations of Table-1 through Table-56 can be utilized.

By way of an example and not by way of any limitation, the nanoshell can be a boron nitride nanotube, carbon nanotube, Cornell-dot, cubisome, dendrimer (including plant based dendrimer), deoxyribonucleic acid (DNA) origami nanostructure, exosome, fullerene $C_{60}$ (e.g., malonic acid derivative of $C_{60}$), gold nanoparticles (suitably coated), grapefruit-derived nanovector (GNV), hollow magnetic cage molecule (e.g., $Co_{12}C_6$, $Mn_{12}C_6$ and $Mn_{24}C_{18}$), iron nanoparticle, lipidoid, liposome, mesoporous silica, micelle, nanocrystal, niosome, polysebacic acid (PSA), polysilsesquioxane (PSQ), porous silicon photonic crystal, quantum dot, quantum dot capped with glutathione, ribonucleic acid (RNA) origami nanostructure, self-assembling peptide (or self-assembling protein), solid-lipid nanoparticle, spherical nucleic acid (SNA), synthasome, tubular/tetrahedral structure fabricated/constructed, utilizing DNA/RNA origami process, virus (e.g., tobacco mosaic virus), zein-plant protein and zeolite-1-nanocrystal.

Silk fibroin is biodegradable and biocompatible. For sustained delivery of the bioactive compound(s) in the pharmaceutical formulations of Table-1 through Table-56, the bioactive compound(s) and/or the pharmaceutical formulations of Table-1 through Table-56 can be loaded with silk fibroin.

PREFERRED EMBODIMENTS OF SPECIFICATIONS

In the above disclosed specifications "/" has been used to indicate an "or".

Any example in the above disclosed specifications is by way of an example only and not by way of any limitation. The best mode requirement "requires an inventor to disclose the best mode contemplated by him/her, as of the time he/she executes the application, of carrying out the invention." " . . . [T]he existence of a best mode is a purely subjective matter depending upon what the inventor actually believed at the time the application was filed." See Bayer AG v. Schein Pharmaceuticals, Inc. The best mode requirement still exists under the America Invents Act (AIA). At the time of the invention, the inventor described preferred best mode embodiments of the present invention. The sole purpose of the best mode requirement is to restrain the inventor from applying for a patent, while at the same time concealing from the public preferred embodiments of their inventions, which they have in fact conceived. The best mode inquiry focuses on the inventor's state of mind at the time he/she filed the patent application, raising a subjective factual question. The specificity of disclosure required to comply with the best mode requirement must be determined by the knowledge of facts within the possession of the inventor at the time of filing the patent application. See Glaxo, Inc. v. Novopharm LTD., 52 F.3d 1043, 1050 (Fed. Cir. 1995).

The above disclosed specifications are the preferred best mode embodiments of the present invention. However, they are not intended to be limited only to the preferred best mode embodiments of the present invention. Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention. The inventor of the present invention is not required to describe each and every conceivable and possible future embodiment in the preferred best mode embodiments of the present invention. See SRI Int'l v. Matsushita Elec. Corp. of America, 775F.2d 1107, 1121, 227 U.S.P.Q. (BNA) 577, 585 (Fed. Cir. 1985) (enbanc).

I claim:

1. A transdermal patch for pain management, comprising:
pharmaceutical formulation of

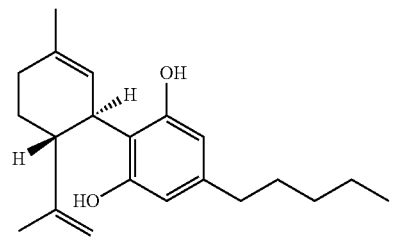 [SMILES: C=C(C)[C@@H]1CCC(C)=C[C@H]1c1c(O)cc(CCCCC)cc1O]

(a) cannabidiol (CBD) or cannabidiol (CBD) pro-drug;
(b) silk fibroin;
(c) *Boswellia serrata* extract; and
(d) a bioactive compound astaxanthin.

2. The transdermal patch according to claim 1, is a single segment transdermal patch.

3. The transdermal patch according to claim 1, comprises: cannabidiol (CBD) or cannabidiol (CBD) pro-drug in microemulsion.

4. The transdermal patch according to claim 1, further comprises: a permeation enhancement compound.

5. A transdermal patch for pain management, comprising:
pharmaceutical formulation of

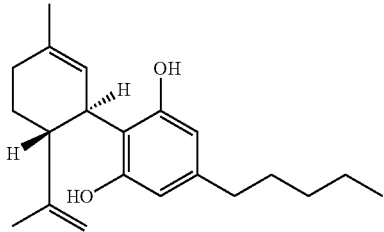

(a) cannabidiol (CBD) or cannabidiol (CBD) pro-drug;

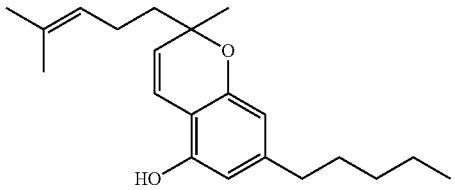 [SMILES: CCCCCc1cc(O)c2c(c1)OC(C)(CCC=C(C)C)C=C2]

(b) cannabichromene (CBC) or cannabichromene (CBC) pro-drug;
(c) silk fibroin;
(d) *Boswellia serrata* extract; and
(e) a bioactive compound astaxanthin.

6. The transdermal patch according to claim 5, is a single segment transdermal patch.

7. The transdermal patch according to claim 5, comprises: cannabidiol (CBD) or cannabidiol (CBD) pro-drug in microemulsion.

8. The transdermal patch according to claim 5, further comprises: a permeation enhancement compound.

9. A transdermal patch for pain management, comprising:
pharmaceutical formulation of

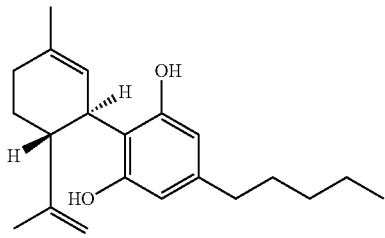 [SMILES: C=C(C)[C@@H]1CCC(C)=C[C@H]1c1c(O)cc(CCCCC)cc1O]

(a) cannabidiol or cannabidiol pro-drug;

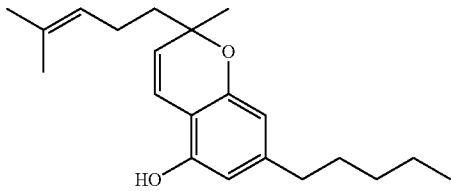 [SMILES: CCCCCc1cc(O)c2c(c1)OC(C)(CCC=C(C)C)C=C2]

(b) cannabichromene or cannabichromene pro-drug;
(c) *Boswellia serrata* extract or capsaicin;
(d) silk fibroin; and
(e) a bioactive compound astaxanthin.

10. A transdermal patch for pain management, comprising:
pharmaceutical formulation of
(a) *Boswellia serrata* extract;
(b) capsaicin;
(c) silk fibroin, and
(d) a bioactive compound astaxanthin.

11. The transdermal patch according to claim 10, is a single segment transdermal patch.

12. The transdermal patch according to claim 10, further comprises: a permeation enhancement compound.

* * * * *